US009242105B2

(12) United States Patent
Brockway et al.

(10) Patent No.: US 9,242,105 B2
(45) Date of Patent: Jan. 26, 2016

(54) CONTROLLED TITRATION OF NEUROSTIMULATION THERAPY

(71) Applicant: Cardiac Pacemakers, Inc., St. Paul, MN (US)

(72) Inventors: Marina V. Brockway, Shoreview, MN (US); Imad Libbus, St. Paul, MN (US); Krzysztof Z. Siejko, Maple Grove, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/268,770

(22) Filed: May 2, 2014

(65) Prior Publication Data

US 2014/0243929 A1    Aug. 28, 2014

Related U.S. Application Data

(60) Continuation of application No. 13/487,877, filed on Jun. 4, 2012, now Pat. No. 8,725,250, which is a continuation of application No. 12/886,328, filed on Sep. 20, 2010, now Pat. No. 8,195,290, which is a division of application No. 11/468,143, filed on Aug. 29, 2006, now Pat. No. 7,801,604.

(51) Int. Cl.
| | |
|---|---|
| *A61N 1/372* | (2006.01) |
| *A61N 1/36* | (2006.01) |
| *A61B 5/024* | (2006.01) |
| *A61B 5/00* | (2006.01) |
| *A61N 1/362* | (2006.01) |

(52) U.S. Cl.
CPC .......... *A61N 1/3727* (2013.01); *A61B 5/02405* (2013.01); *A61B 5/4839* (2013.01); *A61N 1/36114* (2013.01); *A61N 1/36139* (2013.01); *A61N 1/37264* (2013.01); *A61B 5/4035* (2013.01); *A61N 1/362* (2013.01); *A61N 1/36117* (2013.01)

(58) Field of Classification Search
None
See application file for complete search history.

(56) References Cited

U.S. PATENT DOCUMENTS

| | | |
|---|---|---|
| 5,097,833 A | 3/1992 | Campos |
| 5,222,494 A | 6/1993 | Baker, Jr. |

(Continued)

FOREIGN PATENT DOCUMENTS

| | | |
|---|---|---|
| WO | WO-2006101917 A2 | 9/2006 |
| WO | WO-2008027233 A1 | 3/2008 |
| WO | WO-2008027242 A2 | 3/2008 |

OTHER PUBLICATIONS

"U.S. Appl. No. 11/468,143, Non-Final Office Action mailed Oct. 6, 2009", 8 pgs.

(Continued)

*Primary Examiner* — Brian T Gedeon
(74) *Attorney, Agent, or Firm* — Schwegman Lundberg & Woessner, P.A.

(57) ABSTRACT

Described herein are methods and devices that utilize electrical neural stimulation to treat heart failure by modulating a patient's autonomic balance in a manner that inhibits sympathetic activity and/or augments parasympathetic activity. Because other therapies for treating heart failure may also affect a patient's autonomic balance, a device for delivering neural stimulation is configured to appropriately titrate such therapy in either an open-loop or closed-loop fashion.

20 Claims, 5 Drawing Sheets

(56) References Cited

U.S. PATENT DOCUMENTS

| | | |
|---|---|---|
| 6,516,227 B1 | 2/2003 | Meadows et al. |
| 7,069,070 B2 | 6/2006 | Carlson et al. |
| 7,072,711 B2 * | 7/2006 | Girouard et al. ............... 607/3 |
| 7,155,284 B1 | 12/2006 | Whitehurst et al. |
| 7,277,761 B2 | 10/2007 | Shelchuk |
| 7,660,628 B2 | 2/2010 | Libbus et al. |
| 7,801,604 B2 | 9/2010 | Brockway et al. |
| 7,925,342 B2 | 4/2011 | Amurthur et al. |
| 8,195,290 B2 | 6/2012 | Brockway et al. |
| 8,457,734 B2 | 6/2013 | Libbus et al. |
| 8,478,397 B2 | 7/2013 | Libbus et al. |
| 8,725,250 B2 | 5/2014 | Brockway et al. |
| 2002/0116030 A1 | 8/2002 | Rezai |
| 2003/0036773 A1 | 2/2003 | Whitehurst et al. |
| 2003/0040774 A1 | 2/2003 | Terry, Jr. et al. |
| 2004/0077995 A1 | 4/2004 | Ferek-Petric et al. |
| 2004/0215286 A1 | 10/2004 | Stypulkowski |
| 2005/0065553 A1 | 3/2005 | Ben Ezra et al. |
| 2005/0065554 A1 | 3/2005 | KenKnight et al. |
| 2005/0154426 A1 | 7/2005 | Boveja et al. |
| 2006/0089592 A1 | 4/2006 | Kadhiresan et al. |
| 2006/0217772 A1 | 9/2006 | Libbus et al. |
| 2008/0058871 A1 | 3/2008 | Libbus et al. |
| 2008/0058872 A1 | 3/2008 | Brockway et al. |
| 2010/0114226 A1 | 5/2010 | Libbus et al. |
| 2012/0245646 A1 | 9/2012 | Brockway et al. |

OTHER PUBLICATIONS

"U.S. Appl. No. 11/468,143, Notice of Allowance mailed May 18, 2010", 7 pgs.

"U.S. Appl. No. 11/468,143, Response filed Feb. 8, 2010 to Non Final Office Action mailed Oct. 6, 2009", 9 pgs.

"U.S. Appl. No. 11/468,143, Response filed Jul. 16, 2009 to Restriction Requirement mailed Jun. 16, 2009", 9 pgs.

"U.S. Appl. No. 11/468,143, Restriction Requirement mailed Jun. 16, 2009", 10 pgs.

"U.S. Appl. No. 12/886,328, Notice of Allowance mailed Feb. 3, 2012", 8 pgs.

"U.S. Appl. No. 12/886,328, Response filed Jan. 12, 2012 to Restriction Requirement mailed Dec. 12, 2011", 10 pgs.

"U.S. Appl. No. 12/886,328, Restriction Requirement mailed Dec. 12, 2011", 6 pgs.

"U.S. Appl. No. 13/487,877, Notice of Allowability mailed Mar. 4, 2014", 4 pgs.

"U.S. Appl. No. 13/487,877, Notice of Allowance mailed Dec. 30, 2013", 11 pgs.

"Australian Application Serial No. 2007290736, First Examiner Report mailed Aug. 12, 2010", 3 pgs.

"European Application Serial No. 07837091.3, Office Action mailed Feb. 18, 2010", 2 pgs.

"European Application Serial No. 07837091.3, Response filed Aug. 12, 2010 to Office Action mailed Feb. 18, 2010", 12 pgs.

"International Application Serial No. PCT/US2007/018411, Invitation to Pay Fees and Partial International Search Report mailed Nov. 7, 2008", 4 pgs.

"International Application Serial No. PCT/US2007/018411, Search Report mailed Mar. 24, 2009", 6 pgs.

"International Application Serial No. PCT/US2007/018411, Written Opinion mailed Mar. 24, 2009", 10 pgs.

Francis, G. S., et al,, "Acute vasoconstrictor response to intravenous furosemide in patients with chronic congestive heart failure. Activation of the neurohumoral axis", Annals of Internal Medicine, 103(1), (Jul. 1985), 1-6.

Li, M., et al., "Vagal nerve stimulation markedly improves long-term survival after chronic heart failure in rats", Circulation, 109(1), (2004), 120-124.

Libbus, I., et al., "System and Method for Neural Stimulation", U.S. Appl. No. 11/468,135, filed Aug. 29, 2006, 57 pgs.

U.S. Appl. No. 13/908,033, filed Jun. 3, 2012, Systems and Method for Neutal Stimultation.

* cited by examiner

CONTROLLED TITRATION OF NEUROSTIMULATION THERAPY

CLAIM OF PRIORITY

This application is a continuation of and claims the benefit of priority under 35 U.S.C. §120 to U.S. patent application Ser. No. 13/487,877, filed on Jun. 4, 2012, now issued as U.S. Pat. No. 8,725,250, which is a continuation of and claims the benefit of priority under 35 U.S.C. §120 to U.S. patent application Ser. No. 12/886,328, filed on Sep. 20, 2010, now issued as U.S. Pat. No. 8,195,290, which is a divisional of and claims the benefit of priority under 35 U.S.C. §120 to U.S. patent application Ser. No. 11/468,143 filed on Aug. 29, 2006, now issued as U.S. Pat. No. 7,801,604, each of which are hereby incorporated by reference herein in its entirety.

RELATED APPLICATIONS

This application is related to U.S. patent application Ser. No. 11/087,935 filed Mar. 23, 2005, now issued as U.S. Pat. No. 7,660,628 and to U.S. patent application Ser. No. 11/468,135 filed Aug. 29, 2006, now issued as U.S. Pat. No. 8,457,734, the disclosures of which are hereby incorporated by reference in their entirety.

FIELD OF THE INVENTION

This patent application pertains to methods and apparatus for the treatment of cardiac disease with electro-stimulatory therapy.

BACKGROUND

Heart failure (HF) refers to a clinical syndrome in which an abnormality of cardiac function causes a below normal cardiac output that can fall below a level adequate to meet the metabolic demand of peripheral tissues. It can be due to a variety of etiologies with ischemic heart disease being the most common. Heart failure can be treated medically with diuretics to decrease fluid retention and preload, vasodilators to decrease afterload, and inotropic agents to increase myocardial contractility. It has also been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

In patients with heart failure or following a myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

SUMMARY

Described herein are methods and devices that utilize electrical neural stimulation to treat heart failure by modulating a patient's autonomic balance in a manner that inhibits sympathetic activity and/or augments parasympathetic activity. Because other therapies for treating heart failure may also affect a patient's autonomic balance, a device for delivering neural stimulation is configured to appropriately titrate such therapy in either an open-loop or closed-loop fashion.

DETAILED DESCRIPTION

Figure 1:
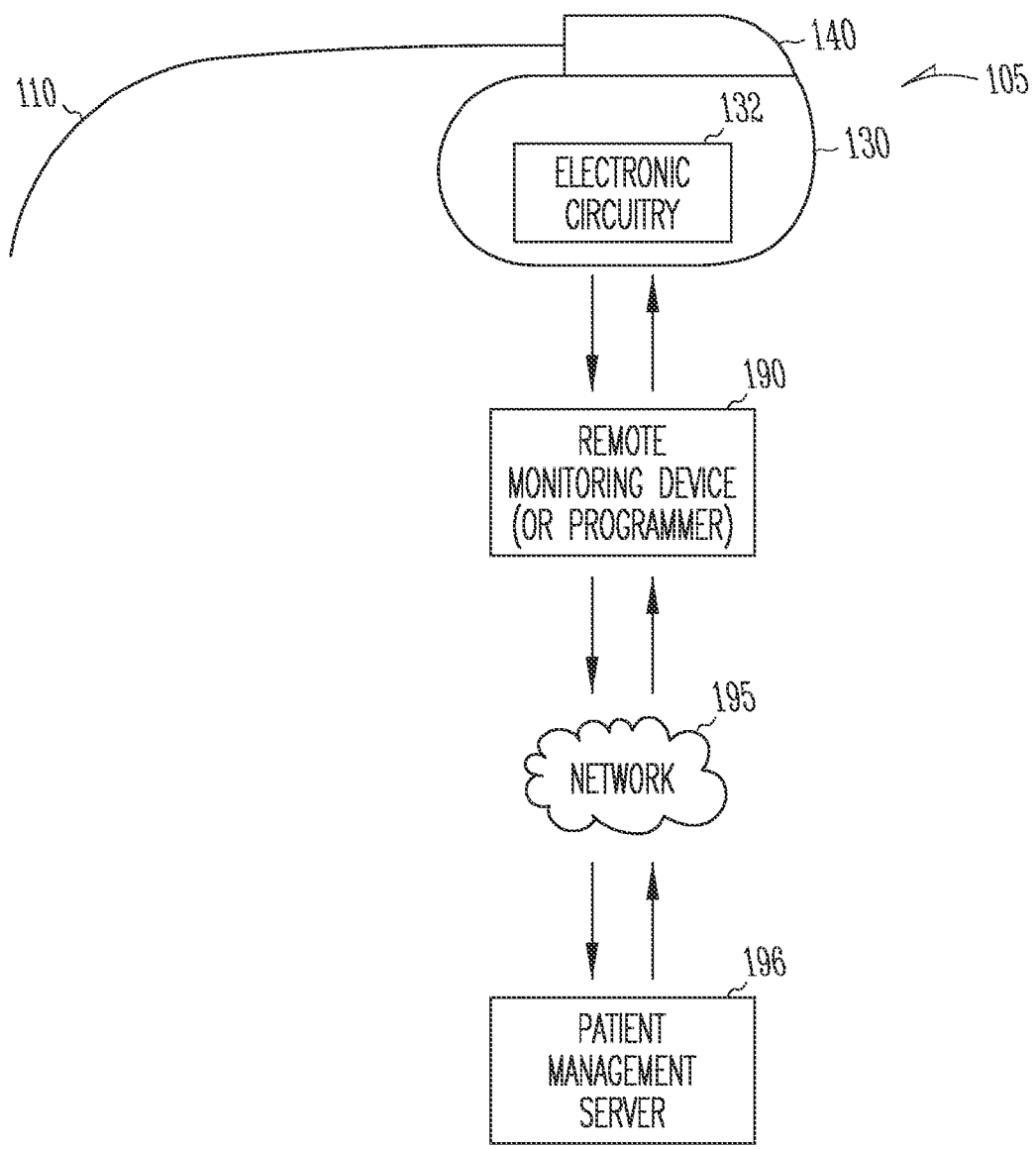
FIG. 1 illustrates a system for delivering neural stimulation.

As noted above, activity of the autonomic nervous system is at least partly responsible for the ventricular remodeling which occurs as a consequence of an MI or heart failure due to other causes. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Described herein are methods and devices that employ electrical neurostimulation to modulate autonomic activity and which allow titration of the neurostimulation therapy in accordance with doses of medication that also affect autonomic activity and/or in accordance with physiological measurements reflective of autonomic activity.

As described below, an implantable medical device may be equipped with a pulse generator for delivering electrical stimulation to one or more selected neural sites via appropriately positioned electrodes. In order to reverse, prevent, or lessen the extent of cardiac remodeling, neural stimulation is applied in a manner that results in parasympathetic stimulation and/or sympathetic inhibition. In addition to its beneficial effects on cardiac remodeling, such neural stimulation can also be beneficial in treating patients with heart failure due primarily to diastolic dysfunction rather than systolic dysfunction, termed diastolic heart failure (DHF). In patients with DHF, the fraction of the blood accumulated during diastolic filling of one or both ventricles that is pumped out during systole, referred to as the ejection fraction, is at or near normal. In these patients myocardial relaxation (lusitropy) is compromised leading to impaired ventricular filling and low cardiac output which is compensated for by increased preload.

Neural stimulation for treating heart failure may be delivered directly to an efferent parasympathetic nerve such as the vagus nerve or to an afferent nerve such as a baroreceptor that causes parasympathetic stimulation and/or sympathetic inhibition via a reflex arc. The vagus nerve provides parasympathetic stimulation to the heart which counteracts the effects of increased sympathetic activity, and stimulation of the vagus nerve at either a pre-ganglionic or post-ganglionic site produces dilation of the coronary arteries and a reduced workload on the heart. Vagal stimulation may be delivered, for example, using an intravascular electrode disposed near the vagus (e.g., in the internal jugular vein) or using a nerve cuff electrode (e.g., placed around the cervical vagus nerve bundle). Baroreceptors are sensory nerve endings located in the heart and vasculature that are stimulated by increased fluid pressure. Stimulation of baroreceptors causes impulses to be relayed via afferent pathways to nuclei in the brainstem that result in parasympathetic activation and sympathetic inhibition. Baroreflex stimulation may be brought about using a nerve cuff electrode placed around the aortic or carotid sinus nerve or using an intravascular electrode disposed near baroreceptors in the heart or pulmonary artery.

Exemplary Device Descriptions

FIG. 1 shows the components of an exemplary system for delivering neural stimulation. An implantable neural stimulation device 105 includes a hermetically sealed housing 130 that is placed subcutaneously or submuscularly in a patient's chest or other convenient location similar to a cardiac pacemaker. The housing 130 may be formed from a conductive metal, such as titanium, and may serve as an electrode for delivering electrical stimulation with a unipolar lead. A header 140, which may be formed of an insulating material, is mounted on the housing 130 for receiving one or more leads 110 which are electrically connected to the circuitry within the housing. Electrical pulse generation circuitry within the housing 130 is connected to a lead 110 which incorporates a bipolar or unipolar electrode at its distal end for stimulating nervous tissue. In one embodiment, the lead 110 is tunneled subcutaneously to a specific pre-ganglionic or post-ganglionic stimulation site near the vagus nerve or an afferent baroreceptor nerve. In another embodiment, the lead 110 is threaded intravascularly to dispose the stimulating electrode(s) near a target nerve. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 105 and enables a clinician to receive data and modify the programming of the controller. A neural stimulation device may be configured to control the delivery of neural stimulation in an open-loop fashion via telemetry or in a closed-loop fashion based upon an assessment of autonomic balance performed by the device. A magnetically or tactilely actuated switch may also be provided that allows the patient to initiate or stop the delivery of neural stimulation pulses. A remote monitoring device that communicates via telemetry with the device 105 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 2:
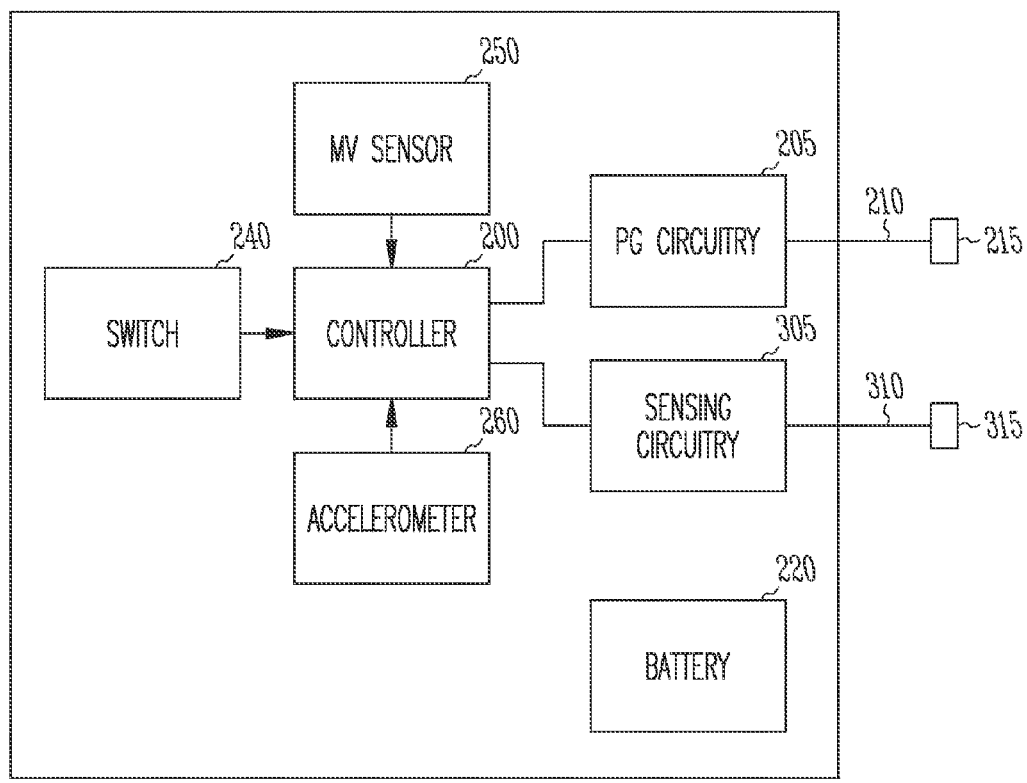
FIG. 2 is a block diagram of an implantable device for delivering neural stimulation.

FIG. 2 is a system diagram of exemplary electronic components contained within the housing 130 of the neural stimulator. A programmable electronic controller 200 is interfaced to pulse generation circuitry 205 and controls the output of neural stimulation pulses. The controller may also be interfaced to sensing circuitry for sensing cardiac activity or other physiological variables. The controller 200 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. The controller includes circuitry for generating clock signals used to keep track of lapsed time intervals and deliver neural stimulation in accordance with a defined schedule. The pulse generation circuitry 205 may be similar to that used in cardiac pacemakers and delivers electrical stimulation pulses to a neural stimulation electrode 215 (or electrodes in the case of a bipolar lead) via the lead 210. A battery 220 also contained within the housing provides power to the device. A magnetically or tactilely actuated switch 240 interfaced to the controller 200 allows the patient to initiate and/or stop the delivery of neural stimulation pulses. Once begun, the neural stimulation pulses may continue to be delivered for a predetermined length of time or according to a predetermined schedule. The pulse frequency, pulse width, pulse amplitude, pulse polarity, and bipolar/unipolar stimulation configuration in this embodiment are programmable parameters, the optimal settings of which depend upon the stimulation site and type of stimulation electrode. The device may also be equipped with different sensing modalities for sensing physiological variables affected by neural stimulation. The device may then be programmed to use these variables in controlling the delivery of neural stimulation. The device in FIG. 2 includes sensing circuitry 305 connected to an electrode 315 (or electrodes in the case of a bipolar lead) via the lead 310 which may be intravenously disposed in the heart for detecting cardiac electrical activity. The sensing circuitry 305 allows the device to measure heart rate and to compute parameters derived therefrom such as heart rate variability or heart rate turbulence for use in controlling the delivery of neural stimulation. Separate sensing channels may be provided for detecting both atrial and ventricular beats. For example, vagal stimulation slows the heart rate, and the device may be programmed to titrate the level of neural stimulation delivered in response to a detected change in heart rate. The device may also be programmed to titrate the level of neural stimulation delivered in response to a detected change in one or more other sensed or derived variables affected by the neural stimulation. For example, as neural stimulation may affect respiratory rate, the device also includes a minute ventilation sensor 250 and may be programmed to similarly titrate the level of neural stimulation delivered in response to a detected change in respiratory rate. An accelerometer 260 is also interfaced to the controller which enables the device to detect the patient's activity level as well as heart sounds, the intensity of which may be reflective of myocardial contractility. A pressure sensor could also be used for this purpose by measuring arterial dP/dt during systole. The accelerometer 260 may also be used to detect coughing brought about by vagal stimulation. The device may then be programmed so that neural stimulation is decreased or stopped if persistent coughing by the patient is detected.

Figure 3:
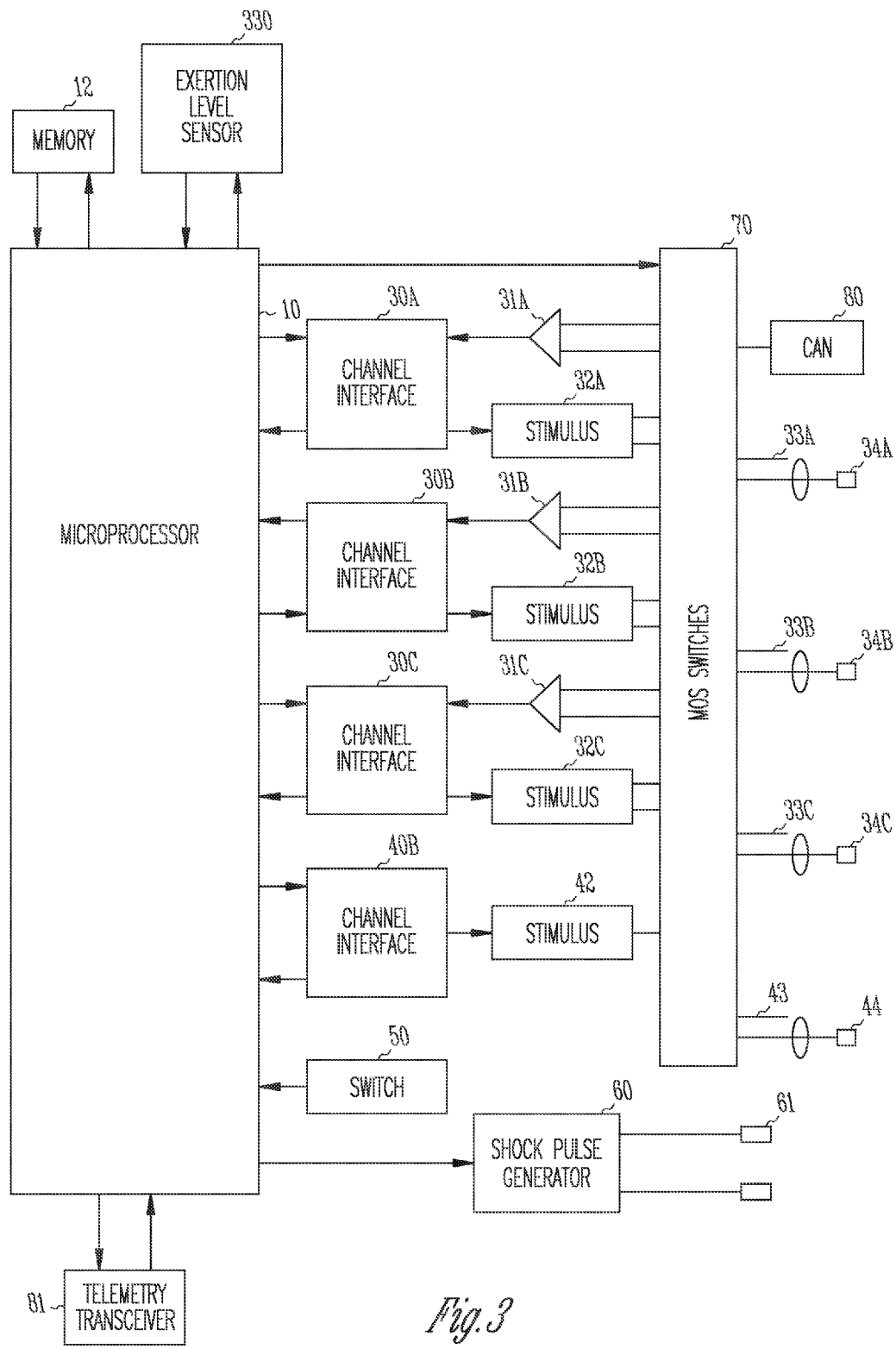
FIG. 3 is a block diagram of an implantable cardiac device with the capability of delivering neural stimulation.

A neural stimulator may also be incorporated into an implantable cardiac device configured to deliver conventional bradycardia pacing, anti-tachyarrhythmia therapy, and/or CRT. As noted above, CRT may beneficially treat some heart failure patients who suffer conduction deficits and consequent cardiac dyssynchrony. It has also been found that CRT can be beneficial in reducing the deleterious ventricular remodeling which can occur in post-MI and heart failure patients as a result of changes in the distribution of wall stress experienced by the ventricles during the cardiac pumping cycle when CRT is applied to pre-excite particular areas of the ventricles. By pacing one or more sites in a ventricle, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur. FIG. 3 illustrates an embodiment of a neural stimulator that is incorporated into an implantable cardiac rhythm management device which has cardiac pacing and/or cardioversion/defibrillation functionality. The device is battery-powered and equipped with multiple sensing and pacing channels which may be physically configured to sense and/or pace the atria or the ventricles in a variety of pacing modes including conventional bradycardia pacing and cardiac resynchronization pacing. The controller of the device includes a microprocessor 10 which communicates with a memory 12 via a bidirectional data bus. Shown in FIG. 3 are three exemplary sensing and pacing channels designated "a" through "c" comprising bipolar leads with ring electrodes 34a-c and tip electrodes 33a-c, sensing amplifiers 31a-c, pulse generators 32a-c, and channel interfaces 30a-c. Each channel thus includes a pacing channel made up of the pulse generator connected to the electrode and a sensing channel made up of the sense amplifier connected to the electrode. The channel interfaces 30a-c communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively. The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 80 serving as a ground electrode. A shock pulse generator 60 is also interfaced to the controller for delivering a defibrillation shock via a pair of shock electrodes 61 to the atria or ventricles upon detection of a shockable tachyarrhythmia. A minute ventilation sensor 330 or other sensor that measures a parameter related to metabolic demand enables the controller to adapt the pacing rate in accordance with changes in the patient's physical activity. A telemetry transceiver 81 is also provided which enables the controller to communicate with an external programmer or remote monitor.

A neural stimulation channel is incorporated into the device for delivering neural stimulation which includes a bipolar lead with a ring electrode 44 and a tip electrode 43, a pulse generator 42, and a channel interface 40. Other embodiments may use unipolar leads in which case the neural stimulation pulses are referenced to the can or another electrode. Also, in certain embodiments, a cardiac pacing channel may be used as a neural stimulation channel with an appropriately disposed electrode(s). The pulse generator for the neural stimulation channel outputs a train of neural stimulation pulses that may be varied by the controller as to amplitude, frequency, pulse width, and duty-cycle. A magnetically or tactilely actuated switch 50 for initiating (or stopping) delivery of neural stimulation may be incorporated into the implantable cardiac device such as shown in FIG. 3. The switch 50 may be operated by the patient similar to the operation of the embodiment illustrated in FIG. 2. Either instead of, or in addition to, a magnetically or tactilely actuated switch, neural stimulation may be triggered automatically according to a defined schedule or upon the sensing of a particular entry condition by the implantable device utilizing its available sensing modalities. Once automatic delivery of neural stimulation is begun, the device may be configured so that the patient may stop the stimulation by actuating switch 50. The device may also be configured so that neural stimulation is stopped upon sensing a specified exit condition utilizing its available sensing modalities.

Figure 4:
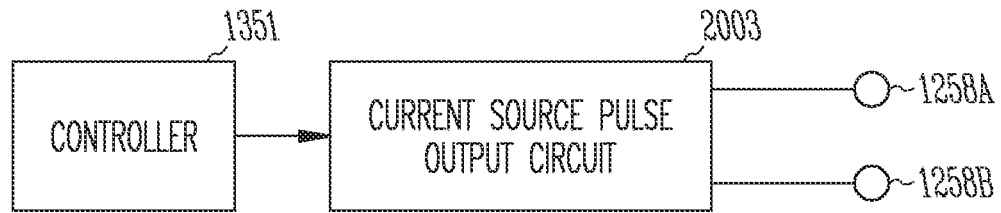
FIGS. 4 and 5 illustrate different embodiments of circuitry for delivering neural stimulation pulse trains.
Figure 5:
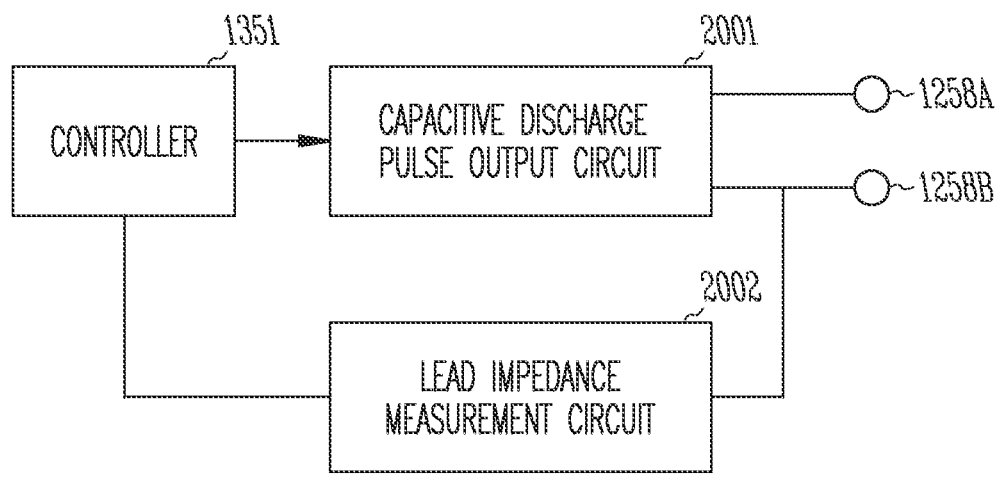

FIGS. 4 and 5 illustrate different embodiments of circuitry for delivering stimulation pulse trains as described above such as the pulse generator 42 in FIG. 3 and the pulse generator 205 in FIG. 2. In FIG. 4, a current source pulse output circuit 2003 outputs current pulses between stimulation electrodes 1258A and 1258B in accordance with command inputs from the controller 1351. The command inputs from the controller which may be programmed by a user specify the frequency of the pulses, pulse widths, current amplitude, pulse polarity, and whether unipolar or bipolar stimulation is to be delivered. FIG. 5 illustrates another embodiment in which a capacitive discharge pulse output circuit 2001 is used to output voltage pulses between stimulation electrodes 1258A and 1258B in accordance with command inputs from the controller 1351. In this embodiment, the command inputs from the controller which may be programmed by a user specify the frequency of the pulses, pulse widths, voltage amplitude, pulse polarity, and whether unipolar or bipolar stimulation is to be delivered. In order for the controller to specify a voltage amplitude that results in a desired current amplitude for the pulses, the lead impedance may be measured by lead impedance measurement circuit 2002. The output capacitor of the pulse output circuit may then be charged to the appropriate voltage for each pulse. In order to monitor the lead impedance, the controller is programmed to periodically, or upon command from a user via telemetry, charge the output capacitor to a known voltage level, connect the output capacitor to the stimulation leads to deliver a stimulation pulse, and measure the time it takes for the capacitor voltage to decay by a certain amount (e.g., to half of the initial value). In order to minimize patient discomfort, the lead impedance procedure should be performed using as low a voltage as possible. In one embodiment, the controller is programmed to use a first voltage amplitude (e.g., 1 volt) and then compare the measurement count (i.e., the capacitor decay time) to a specified minimum value CntZMin. If the measurement count is below CntZMin, the current delivered during the test is deemed too small for the measurement to be accurate. A second measurement pulse is then delivered at a higher second voltage (e.g., 2 volts). If that count is again below CntZMin, a third measurement pulse is delivered at a still higher third voltage (e.g., 4 volts). With a typical stimulation lead, this procedure limits the measurement current to between roughly 1 mA and 0.6 mA.

Controlled Delivery of Neural Stimulation

Figure 6:
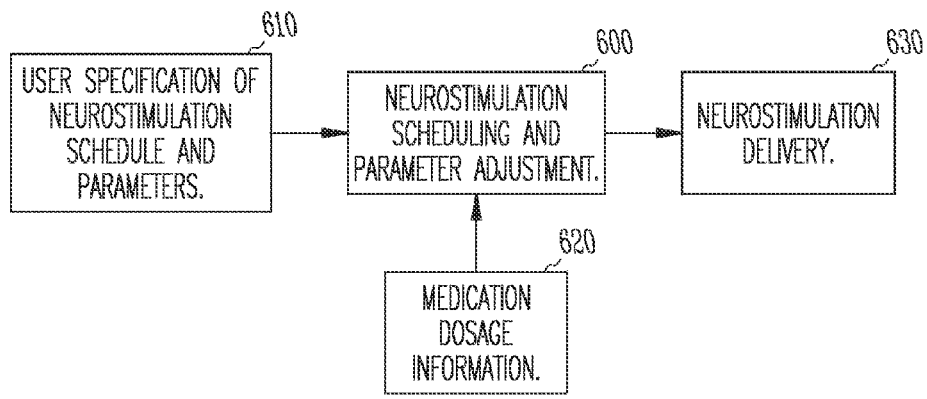
FIG. 6 illustrates an exemplary algorithm for open-loop control of neural stimulation delivery.

A patient's response to a particular level of neural stimulation may vary over time due to a variety of factors. For example, a patient's autonomic balance may vary in accordance with circadian rhythms. The neural stimulator may be programmed to schedule delivery of neural stimulation in accordance with the patient's circadian rhythms for maximum beneficial effect. A patient with HF also typically takes medications that affect autonomic balance such as beta-blockers that diminish sympathetic stimulation and diuretics that may augment sympathetic stimulation with the release of norepinephrine brought about by stimulation of the rennin-angiotensin system. The device may be programmed to titrate the delivery of neural stimulation by scheduling such delivery and/or adjusting the level of the neural stimulation delivered in an open-loop manner that takes the effects of such medications into account. FIG. 6 illustrates an exemplary algorithm that could be executed by the device controller. Block 600 represents a routine for the scheduling of neurostimulation delivery by the device and appropriate adjustment of stimulation parameters such as pulse amplitude and frequency. Block 610 represents user specification of the stimulation schedule and parameters, and block 630 represents the routine executed by the device to deliver the neurostimulation. Block 620 represents medication dosage information that is input to the device for use by the scheduling and parameter adjustment routine. For example, the device could be programmed to cease or reduce the level of vagal or baroreceptor neural stimulation at the time or times of the day when a beta-blocker is taken by the patient (or is expected to have its maximum effect). Similarly, the device could be programmed to increase the level of vagal or baroreceptor neural stimulation at the time or times of the day when a diuretic is taken by the patient (or when it is expected to have its maximum sympathetic effect). Information as to the times at which the patient takes particular medications could be entered by a clinician or the patient via telemetry. Alternatively, an electronic pill counter could transmit the information to the device via telemetry.

Figure 7:
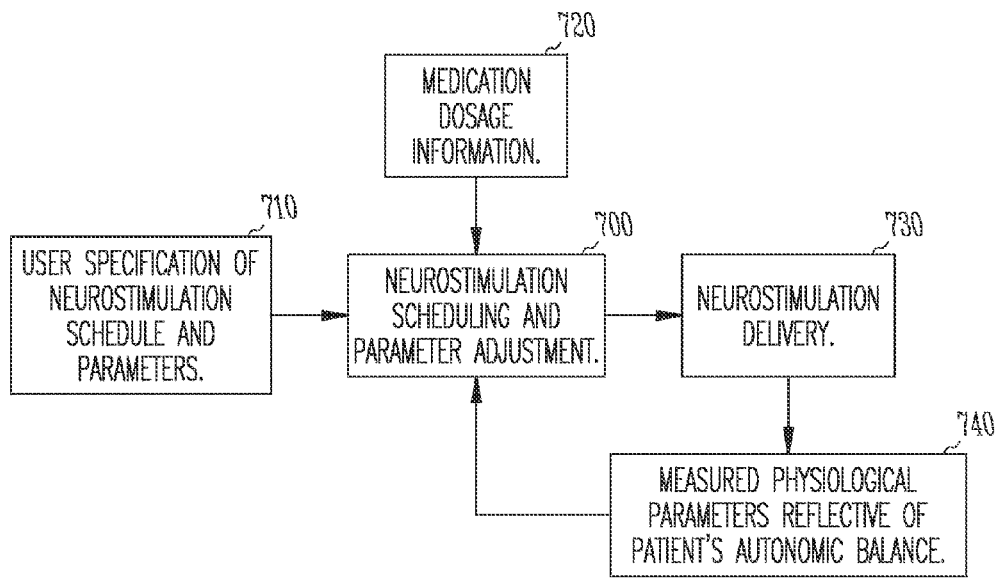
FIG. 7 illustrates an exemplary algorithm for closed-loop control of neurostimulation delivery.

In another embodiment, the neurostimulator is programmed to control the delivery of neural stimulation in a closed-loop manner in accordance with sensed or derived physiological variables that are reflective of a patient's autonomic balance. Controlling the delivery of neural stimulation in a closed-loop instead of an open-loop manner as described above allows the device to take into account various factors that affect a patient's autonomic balance. Such factors include the patient's individualized response to medications, non-compliance in taking medications, different drug interactions, and other factors not related to medication that may cause a patient's autonomic balance to vary during the day. Delivering neural stimulation in accordance with a patient's detected autonomic balance not only results in the patient receiving an optimal amount of neural stimulation but also conserves battery power by not wasting energy to deliver stimulation when it is not needed. As discussed above, the device may be programmed to titrate the amount of neural stimulation by scheduling such delivery and/or adjusting the level of the neural stimulation delivered in accordance with measured physiological variables such as heart rate, count of premature ventricular contractions (PVC), heart rate turbulence, heart rate variability, intrinsic P-R interval, respiratory rate, activity level, or myocardial contractility as determined from sensed heart sounds or measured pulse pressure change (dP/dt). For example, the amount of vagal or baroreceptor neural stimulation delivered by the device could be increased in response to a detected increase in heart rate, heart rate turbulence, respiratory rate, myocardial contractility, or P-R interval that reflect an increase in sympathetic tone. The device could similarly reduce the amount of stimulation in response to a detected decrease in those variables. The device may also be programmed to also use medication dosage information as described above in conjunction with the sensed physiological variables to control the delivery of neural stimulation. For example, a determination of autonomic balance based upon one or more sensed physiological variables could be used to confirm a patient's response to medication before adjusting the amount of neural stimulation to be delivered in accordance with an expected response to the medication. FIG. 7 illustrates an exemplary algorithm that could be executed by the device controller to effect closed-loop control of neurostimulation delivery. Block 700 represents a routine for the scheduling of neurostimulation delivery by the device and appropriate adjustment of stimulation parameters such as pulse amplitude and frequency. Block 710 represents user specification of the stimulation schedule and parameters, and block 730 represents the routine executed by the device to deliver the neurostimulation. Block 720 represents medication dosage information that is input to the device for use by the scheduling and parameter adjustment routine. Block 740 represents the measuring or deriving of one or more physiological variables that are reflective of the patient's autonomic balance and are affected by the neurostimulation. The scheduling and parameter adjustment routine then takes the assessment of autonomic balance into account in delivering neurostimulation. In certain embodiments, data gathered by the device in performing the assessment of autonomic balance is transmitted to a remote monitor via an RF telemetry link. The remote monitor may record the data for later analysis (e.g., trending) by a clinician or computer algorithm and/or transmit it to another location over a network such as the internet.

Another means for assessing the autonomic balance of a patient is spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity, especially if physical activity is low. An LF/HF ratio which exceeds a specified threshold value may be taken as an indicator that cardiac function is not adequate. A device with cardiac sensing capability can be programmed to determine the LF/HF ratio by analyzing data received from its atrial or ventricular sensing channels. The intervals between successive atrial or ventricular senses, referred to as beat-to-beat or BB intervals, can be measured and collected for a period of time or a specified number of beats. The resulting series of BB interval values is then stored as a discrete signal and analyzed to determine its energies in the high and low frequency bands as described above. Techniques for estimating the LF/HF ratio based upon interval data are described in commonly assigned U.S. Pat. No. 7,069,070 and patent application Ser. No. 10/669,170 filed Sep. 23, 2003, the disclosures of which are hereby incorporated by reference. A neurostimulator device may be programmed to titrate the amount of neural stimulation delivered by scheduling such delivery and/or adjusting the level of the neural stimulation delivered in accordance with the estimated LF/HF ratio. The device may thus increase vagal or baroreceptor stimulation when the LF/HF ratio increases above a specified threshold and/or decrease vagal or baroreceptor stimulation when the LF/HF ratio decreases below another specified threshold. The specified thresholds for the LF/HF ratio may be predetermined values or may be derived by the device from monitoring the patient's LF/HF ratio over time and specifying the thresholds relative to a baseline value. In an alternative embodiment, the device may be equipped with a sensing channel for directly measuring autonomic balance by measuring electrical activity in sympathetic and parasympathetic nerves.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering neurostimulation to a patient, comprising:
    a pulse generator for outputting neurostimulation pulses and for connecting to one or more stimulation electrodes to deliver electrical stimulation to one or more selected neural sites the produce parasympathetic stimulation and/or sympathetic inhibition;
    a controller connected to the pulse generator for controlling the output of neurostimulation pulses in accordance with a defined schedule that specifies the times of day the neurostimulation pulses are to be delivered and in accordance with one or more stimulation parameters;
    a sensor interfaced to the controller for sensing a physiological variable reflective of a patient's autonomic balance;
    a telemetry unit interfaced to the controller, wherein the controller is programmed to receive medication dosage information via telemetry that includes the time or times of day that a medication affecting the patient's autonomic balance is to be taken; and,
    wherein the controller is programmed to adjust the schedule for delivering neurostimulation in accordance with received medication dosage information after confirming that the medication has had its expected effect on the patient's autonomic balance as reflected by the sensed physiological variable.

2. The device of claim 1 wherein the controller is further programmed to modify the one or more stimulation parameters in accordance with the medication dosage information.

3. The device of claim 1 wherein the controller is programmed to reduce the amount of neurostimulation delivered when the patient takes a dose of a beta-blocker.

4. The device of claim 1 wherein the controller is programmed to increase the amount of neurostimulation delivered when the patient takes a dose of a diuretic.

5. The device of claim 1 wherein the controller is programmed to receive medication dosage information from an electronic pill counter.

6. The device of claim 1
    wherein the controller is programmed to adjust the amount of neurostimulation delivered in accordance with a determination of the patient's autonomic balance.

7. The device of claim 6 wherein the controller is programmed to adjust the amount of neurostimulation delivered in accordance with the patient's measured heart rate.

8. The device of claim 6 wherein the controller is programmed to:
    measure and collect time intervals between successive intrinsic beats, referred to as a BB interval, and storing the collected intervals as a discrete BB interval signal, filter the BB interval signal into defined high and low frequency bands, and determine the signal power of the BB interval signal in each of the low and high frequency bands, referred to LF and HF, respectively; and,
    compute an LF/HF ratio and assess autonomic balance by comparing the LF/HF ratio to a specified threshold value; and,
    adjust the amount of neurostimulation delivered in accordance with the patient's autonomic balance.

9. The device of claim 8 wherein the controller is programmed to assess autonomic balance in accordance with a measured activity level.

10. The device of claim 9 wherein the sensor is an accelerometer.

11. A method for delivering neurostimulation to a patient, comprising:
    implanting an implantable device to deliver neurostimulation pulses to a selected neural site that produces parasympathetic stimulation and/or sympathetic inhibition;
    programming the implantable device to deliver neurostimulation pulses in accordance with a defined schedule that specifies the times of day the neurostimulation pulses are to be delivered and in accordance with one or more stimulation parameters;

programming the implantable device to sense a physiological variable reflective of the patient's autonomic balance;

programming the implantable device to receive medication dosage information via telemetry that includes the time or times of day that a medication affecting the patient's autonomic balance is to be taken; and, programming the implantable device to adjust the schedule for delivering neurostimulation in accordance with received medication dosage information after confirming that the medication has had its expected effect on the patient's autonomic balance as reflected by the sensed physiological variable.

12. The method of claim 11 further comprising programming the implantable device to modify the stimulation parameters in accordance with the medication dosage information.

13. The method of claim 11 wherein the selected neural site is the vagus nerve or a baroreceptor of a patient and further comprising programming the implantable device to reduce the amount of neurostimulation delivered when the patient takes a dose of a beta-blocker.

14. The method of claim 11 wherein the selected neural site is the vagus nerve or a baroreceptor of a patient and further comprising programming the implantable device to increase the amount of neurostimulation delivered when the patient takes a dose of a diuretic.

15. The method of claim 11 further comprising programming the implantable device to receive medication dosage information from an electronic pill counter.

16. The method of claim 11 further comprising:

programming the implantable device to adjust the amount of neurostimulation delivered in accordance with a determination of the patient's autonomic balance.

17. The method of claim 11 further comprising programming the implantable device to adjust the amount of neurostimulation delivered in accordance with the patient's measured heart rate.

18. The method of claim 11 further comprising programming the implantable device to:

measure and collect time intervals between successive intrinsic beats, referred to as a BB interval, and storing the collected intervals as a discrete BB interval signal, filter the BB interval signal into defined high and low frequency bands, and determine the signal power of the BB interval signal in each of the low and high frequency bands, referred to LF and HF, respectively; and, compute an LF/HF ratio and assess autonomic balance by comparing the LF/HF ratio to a specified threshold value; and, adjust the amount of neurostimulation delivered in accordance with the patient's autonomic balance.

19. The method of claim 18 further comprising programming the implantable device to assess autonomic balance in accordance with a measured activity level.

20. The method of claim 19 further comprising measuring activity level with an accelerometer.

* * * * *